United States Patent
Ghassemi

Patent Number: 5,993,440
Date of Patent: Nov. 30, 1999

[54] NON-INVASIVE LASER CUTTING DEVICE AND METHOD

[76] Inventor: Faramarz Frank Ghassemi, 6553 Timber Ct., San Jose, Calif. 95120

[21] Appl. No.: 09/027,145

[22] Filed: Feb. 20, 1998

Related U.S. Application Data

[60] Provisional application No. 60/062,062, Oct. 16, 1997.

[51] Int. Cl.$^6$ .............. A61N 5/00; A61B 17/36; B26B 19/44
[52] U.S. Cl. ................................. 606/9; 30/41.5
[58] Field of Search ................... 606/9, 13, 16, 606/17, 27, 28, 32, 36, 37, 45, 48, 51; 30/41.5, 41.6

[56] References Cited

U.S. PATENT DOCUMENTS

| | | |
|---|---|---|
| D. 368,962 | 4/1996 | Tahriri . |
| 3,693,623 | 9/1972 | Harte et al. ................... 606/9 |
| 4,498,474 | 2/1985 | Chalmers et al. ............ 606/36 |
| 4,617,926 | 10/1986 | Sutton ......................... 606/9 |
| 4,784,136 | 11/1988 | Klein .......................... 606/36 |
| 5,182,857 | 2/1993 | Simon ......................... 30/34.05 |
| 5,221,280 | 6/1993 | Gross et al. ................. 606/36 |
| 5,364,394 | 11/1994 | Mehl ........................... 606/36 |
| 5,376,088 | 12/1994 | Glaros ......................... 606/36 |
| 5,419,344 | 5/1995 | Dewitt . |
| 5,425,728 | 6/1995 | Tankovich ................... 606/9 |
| 5,533,266 | 7/1996 | Kelman ....................... 30/122 |
| 5,595,568 | 1/1997 | Anderson .................... 606/9 |
| 5,606,798 | 3/1997 | Kelman ....................... 30/41.5 |
| 5,662,894 | 9/1997 | McManus . |
| 5,820,625 | 10/1998 | Izawa et al. ................. 606/9 |

OTHER PUBLICATIONS

Pages of Computer Printout Containing Abstracts of Patents to Kelman No. EP 96102708; GB 09502064; GB 0950220; GB 09200426; EP 96102708A; GB 09502064W; GB 09501220W; GB 09200426W.

Primary Examiner—Linda C. M. Dvorak
Assistant Examiner—Sonya C Harris-Ogugua
Attorney, Agent, or Firm—Charles E. Wands

[57] ABSTRACT

A hand-held, non-invasive cutting device is configured to cut a fiber-like element, such as animal or human hair projecting from the surface of a medium, such as body skin, without exposing the user to the cutting beam. The device exterior is shaped to be readily placed against the surface of the body and has an aperture that accommodates passage of the hair to be cut into an interior region of the housing. The housing includes an optical energy beam director that directs a beam of optical energy, such as a laser beam generated by an external or internal laser, through an interior cutting zone, and onto the inserted element, thereby severing or vaporizing the element. Because the laser beam is aligned with and parallel to the longitudinal direction of the cutting window, then regardless of where it is inserted in the cutting window, the element will be cut by the laser beam. In addition, the beam cannot exit the cutting window, so that the invention is non-invasive and safe for consumer use.

16 Claims, 3 Drawing Sheets

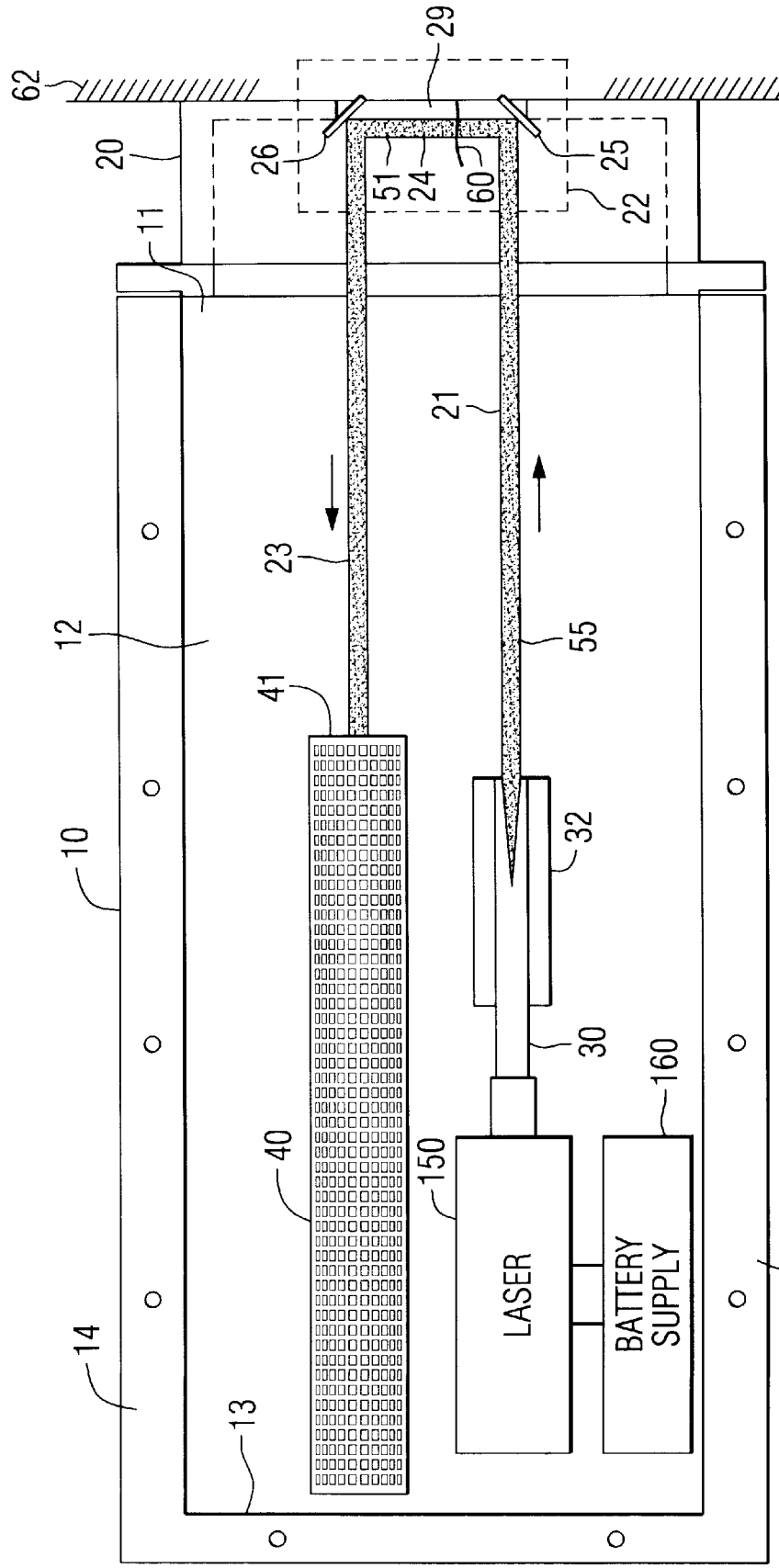

NON-INVASIVE LASER CUTTING DEVICE AND METHOD

CROSS-REFERENCE TO RELATED APPLICATION

The present application claims the benefit of previously filed co-pending Provisional patent application, Ser. No. 60/062,062, filed Oct. 16, 1997.

FIELD OF THE INVENTION

The present invention relates to energy beam devices for cutting or severing fiber-like elements of relatively small cross-section that project from the surface of a medium, for example human or animal hair, without subjecting the underlying surface to potential impingement and damage/injury by the energy beam. The invention particularly relates to the use of a laser beam to cut human or animal hair and the like, while preventing the beam from impinging upon any portion of the subject, such as skin, eyes, etc., other than the element being cut.

BACKGROUND OF THE INVENTION

Conventional methods of cutting or removing relatively fine fiber-like elements, such as but not limited to human and animal hair, clothing and carpet threads and the like from a support medium, such as body skin, clothing, matting etc. include both mechanical schemes, such as electric shavers, and chemical treatments, such as dissolving creams and the like. In addition, there are a number of laser hair removal devices that direct laser energy into the surface of the skin from which the hair, for the purpose of causing the hair follicle to absorb energy and thereby effectively destroy the hair root. As such, these laser schemes proposals are potentially harmful to humans and animals.

In the first place, like chemical treatments (and in some instances mechanical razors), these systems may be undesirably invasive, as their functionality is to penetrate/damage skin tissue (rather than simply cut the hair projecting from a follicle in the skin). Secondly, since they are configured to direct the laser beam directly upon the skin, they are 'open' systems, and expose the subject (as well as the operator) to the potential danger of having the laser beam incident upon a portion of the body, such as the eyes, other than the (hair follicle) region of interest. In addition, present laser hair removal systems require the skill of a medical professional, such as a plastic surgeon or trained nurse.

SUMMARY OF THE INVENTION

In accordance with the present invention, drawbacks of conventional shaving schemes, such as those described above, are effectively obviated by a new and improved device and method for using an optical energy (e.g., laser) beam to cut relatively small cross-section material, such as human or animal hair, without subjecting the underlying skin or any other portion of the subject to impingement and potential damage by the laser beam.

For this purpose, the non-invasive energy beam-based cutting device in accordance with the present invention comprises a housing to which a cutting edge enclosure is attached. To facilitate manipulation by a user, the integrated cutting device is preferably configured and so that it may be readily hand-held. The housing has an interior cavity in which a laser beam-supplying optical fiber or other light guide and a light trap are installed. The optical fiber, which can be and is protected by a surrounding sleeve or sheath, is coupled to receive the output beam generated by a laser that may be mounted either with the housing cavity proper or externally thereto.

When installed within the housing cavity, the laser may be powered by batteries mounted within a housing battery compartment. The use of an externally mounted laser has the advantage that it reduces the size of the cutting device, and also allows the laser to be independently powered and cooled. This may be preferred for very high optical power density (e.g., industrial) applications, whereas an internally installed, battery-powered laser lends itself to consumer uses, such as personal cosmetic products.

Within the housing the optical fiber output may be focused and/or collimated by optical components, such as but not limited to lenses, mirrors, prisms and the like, mounted adjacent to a forward open end of the housing and is aligned with an incident laser beam path of a set of beam-directing optics supported within the cutting edge enclosure. The laser may have an output power density on the order of several thousands of watts per $cm^2$ to several megawatts per $cm^2$, which is more than sufficient to vaporize material, such as hair, fibers and the like, that are inserted into a cutting window or aperture into a cutting zone. The wavelength of the laser is selected to maximize cutting efficiency.

The light trap is mounted with its open, light beam-receiving end facing the forward open end of the housing, so that it is aligned with the return beam path of the beam-directing optics. The light trap absorbs the laser beam traveling along a return path of the beam-directing optics after it has passed through the cutting zone and has severed material inserted into the cutting zone, so that no portion of the laser beam will exit the cutting device.

The beam-directing optics may comprise one or more mirrors and one or more associated optical elements, such as lenses, mirrors, prisms and the like, disposed in the path of the beam exiting the end of the optical fiber along the incident beam path. These beam-directing optics are operative to define a beam of a prescribed cross section along a cutting travel path through the cutting zone, and along the return beam path to the light trap.

The cutting window may be formed at a forwardmost end of the cutting edge enclosure and shaped as a generally longitudinal opening having a width sufficient to accommodate the thickness of the fiber-like material such as hair or the like to be severed, but not so large as to allow entry of an underlying support surface from which the material to be severed projects, such as skin, clothing, matting, etc. In addition, the cutting window may be configured as an interrupted surface and/or may include or have an adjacent mesh, screen, grid or the like. Such a structure serves to inhibit the entry of undesirable material or foreign matter into the housing cavity, and also confines and orients the material being cut in a direction that is generally transverse to the laser beam.

The beam-directing optics are arranged so that the cutting path of the laser beam is substantially aligned with and parallel to the longitudinal direction of the cutting window. This geometry serves two important purposes. On the one hand, maintaining the laser beam parallel to the cutting window is an important safety feature, as it prevents the laser beam from exiting the cutting edge enclosure. This makes the closed laser cutting device of the invention non-invasive. Were the laser beam to exit the cutting window, the user or even another individual might undesirably be subjected to the potential danger of having the laser beam incident upon a portion of the body other than the hair being cut.

In addition, directing the laser beam adjacent and parallel to the entire length of the cutting window ensures that regardless of where it is inserted through the cutting window the material to be cut will always be intercepted by the laser beam. The cutting path may be established by one or more beams from one or multiple energy beam sources (lasers) and may be stationary or scanned.

BRIEF DESCRIPTION OF THE DRAWINGS

FIG. 4 is a diagrammatic interior plan view of a second embodiment of an non-invasive laser beam-based cutting device in accordance with the present invention.

DETAILED DESCRIPTION

Figure 1:
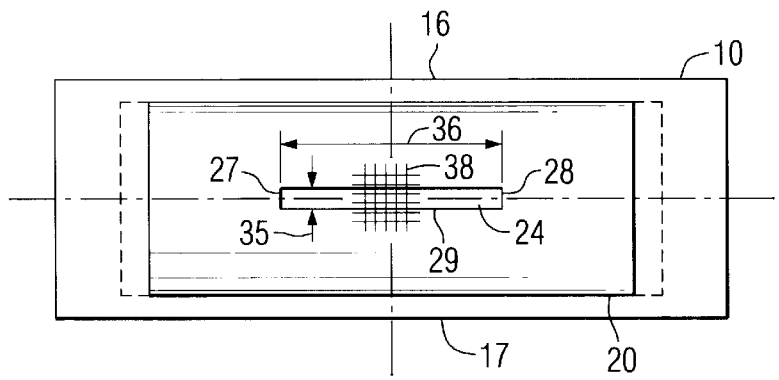
FIG. 1 is a diagrammatic end view of a first embodiment of an non-invasive laser beam-based cutting device in accordance with the present invention.
Figure 2:
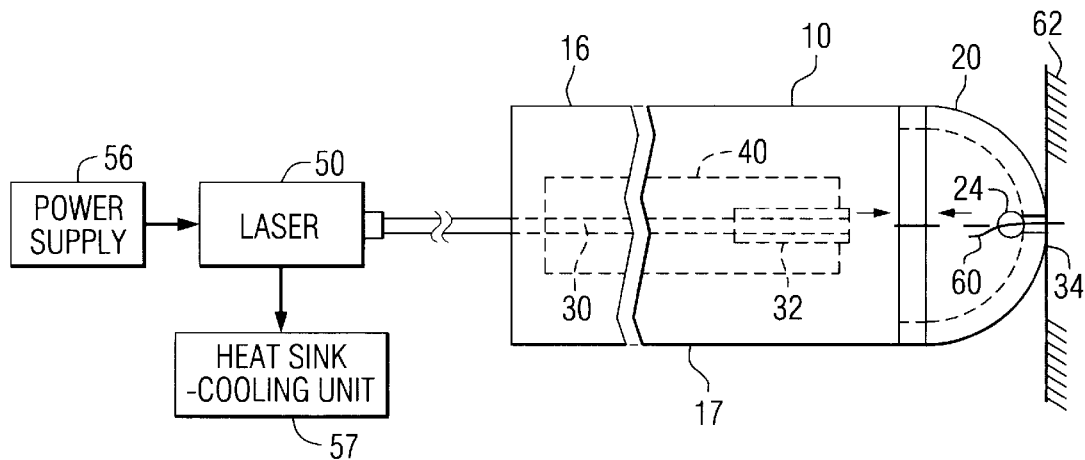
FIG. 2 is a diagrammatic side view of the non-invasive laser beam-based cutting device of FIG. 1.
Figure 3:
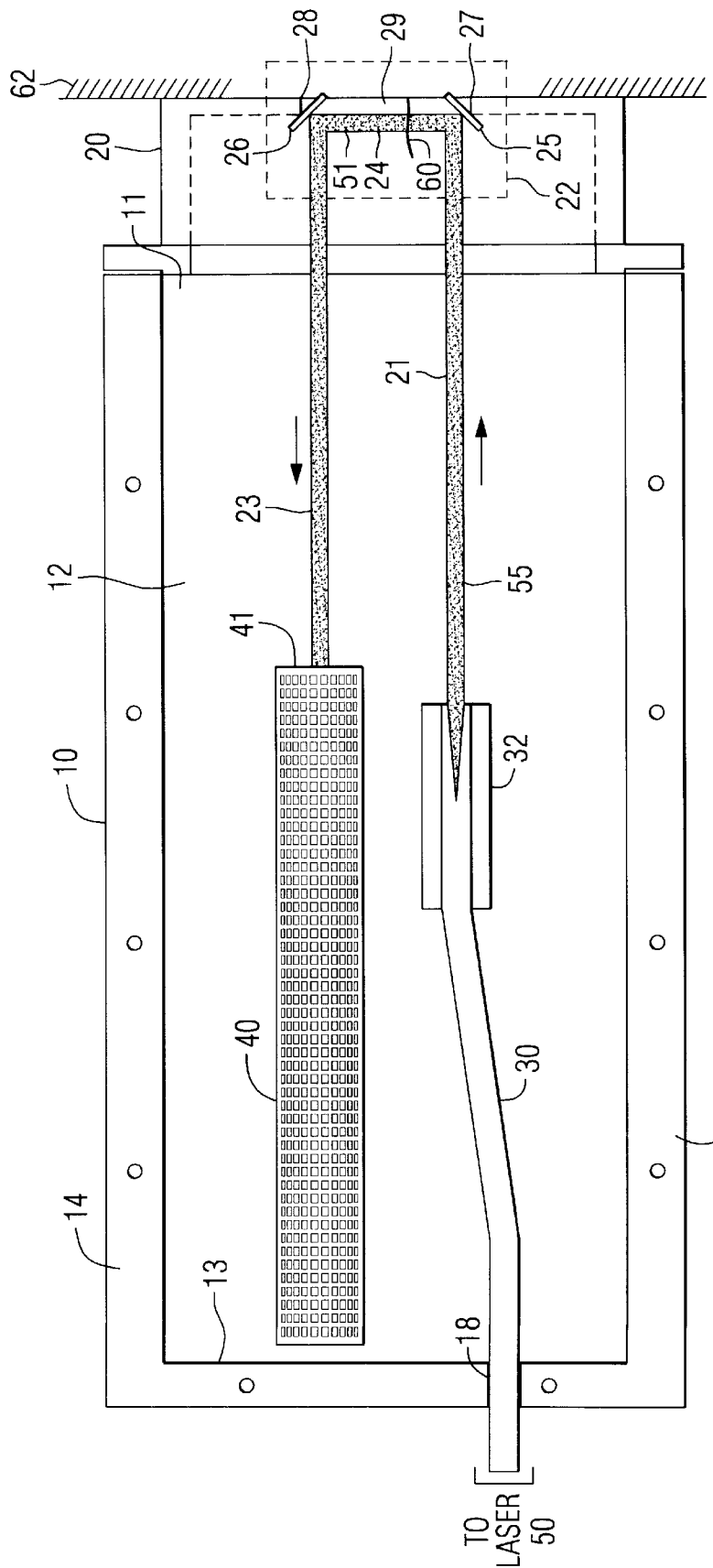
FIG. 3 is a diagrammatic interior plan view of the non-invasive laser beam-based cutting device of FIG. 1.

Attention is now directed to the respective end, side and internal plan views of FIGS. 1–3, which diagrammatically illustrate an embodiment of an non-invasive energy beam-based cutting device in accordance with the present invention. As shown therein the energy beam-based cutting device comprises a generally rectangular-shaped housing 10, to a portion of which, such as a forward open end 11, a cutting edge enclosure 20 is attached. To facilitate comfortable engagement with the skin of a user cutting edge enclosure is preferably of a generally convex or rounded shape.

The housing 10 and the cutting edge enclosure 20 are preferably made of a sturdy material, such as aluminum, stainless steel, ruggedized plastic and the like, and are joined together, as by way of hardware fasteners, to form an integrated unit. To facilitate use, the integrated cutting device is preferably sized and configured, so that it may be readily hand-held.

The housing 10 has an interior cavity 12 bounded by its forward open end 11, a rear wall 13, sidewalls 14 and 15, and top and bottom walls 16 and 17, respectively, and supports therein a laser beam-supplying optical fiber 30, and a light trap 40. The optical fiber 30 may be protected by a surrounding sleeve or sheath, such as a flexible stainless steel jacket, which is coupled to receive the output beam generated by a laser that may be mounted either with the housing cavity proper or externally thereto.

Where the laser is mounted externally of the housing, as in the embodiment of FIGS. 1–3, the jacketed optical fiber 30 may pass through an aperture 18 in the rear housing wall 13, and is coupled to transport a laser beam 55 generated by an external laser 50. The use of an external laser not only reduces the size of the cutting device, but allows the laser to be independently powered and cooled, as shown by power supply 56 and heat sink-cooling unit 57. As pointed out above, the wavelength of the laser is selected to maximize cutting efficiency.

Within the housing 10, the output end of the optical fiber 30 may be focused and/or collimated by one or more optical components, such as, but not limited to, lenses, mirrors, prisms and the like contained within a beam directing and shaping unit 32. In the illustrated embodiment, the beam directing and shaping unit 32 is shown as being mounted adjacent to the forward end 11 of the housing, and is aligned with an incident optical energy (laser) beam path 21 of a set of beam-directing optics 22, which may be supported within the convex cutting edge enclosure 20, as shown. As with each of the individual components of the cutting device of the invention, the laser, optical fiber, protective jacket, and collimator are preferably readily commercially available components, such as those available from Blue Sky Research and Point Source Ltd., Santa Cruz, Calif., 95060, Lumonics Inc, Kanata, Ontario, Canada K2K,1Y3, and Opto Power Corp., Tucson, Ariz. 85706, as non-limiting examples. Depending upon manufacturer, the laser may have an output power density on the order of several thousand of watts per $cm^2$ to several megawatts per $cm^2$, which is more than sufficient to vaporize the material.

The light trap 40 functions to absorb the laser beam 55 traveling along a return path 23 of the beam-directing optics after it has passed through a cutting zone 24, and has severed a hair or the like that has been inserted into the cutting zone, so that no portion of the laser beam will exit the cutting device. For this purpose, as non-limiting examples, the light trap 40 may comprise a generally cylindrical hollow element of light absorbing material, such as a tubular black body having an interior granularly textured carbon black surface, or a series of light baffles that do not permit an entering light beam to escape, thereby absorbing the entering light beam. The light trap 40 is mounted with its open, light beam-receiving end 41 facing the forward open end 11 of the housing 10, so that it is aligned with the return beam path 23 of the beam-directing optics 22.

The beam-directing optics 22 may comprise one or more mirrors and one or more associated lenses, mirrors, prisms, and the like, disposed in the path of the beam exiting the end of the optical fiber 30 along the incident beam path 21, which are operative to define a beam of a prescribed cross section along a cutting or severing travel path 51 through the cutting zone 24, and thereafter along the return beam path 23 to the light trap 40. For this purpose, as a non-limiting simplified example, the diagrammatic interior plan view of FIG. 3 shows beam-directing optics 22 comprising first and second mirrors 25 and 26, respectively mounted at first and second spaced apart edges 27 and 28 of a cutting window or aperture 29 that passes through the wall thickness of generally convex cutting edge enclosure 20.

As shown in the end view of FIG. 1 and the side view of FIG. 2, the cutting window 29 may be formed at a forward-most end 34 of the cutting edge enclosure 20, and may be shaped as a generally longitudinal opening having a width sufficient to accommodate the thickness of the fiber-like material such as hair or the like to be severed, diagrammatically shown at 60, but not so large as to allow entry of an underlying support surface 62 from which the material to be severed projects, such as skin, clothing, matting, etc.

As a non-limiting example, for a human or animal hair cutting application, the cutting window 29 may have a width 35 on the order of one-tenth of an inch, and a length 36 between opposite end edges thereof on the order of a half to three-quarters of an inch. In addition, the cutting window 29 may be configured as an interrupted surface and/or may include or have an adjacent mesh, screen, grid or the like, such as partially shown at 38 in FIG. 1. Such a structure serves to inhibit the entry of undesirable material or foreign matter into the housing cavity 12, and also functions to confine and orient the material being cut in a direction that is generally transverse to the severing travel path 51 of the laser beam 55 through the cutting zone 24. Although not shown, in order to facilitate cleaning of the cutting head and the removal of vaporized hair, a conduit to a microvacuum device, of the type used to remove dust from electronic components and the like, may be terminated adjacent to the cutting window.

As shown in the end view of FIG. 1 and the plan view of FIG. 3, the mirrors 25 and 26 of the beam-directing optics are arranged so that the cutting path 51 of the laser beam is substantially aligned with and parallel to the longitudinal direction of the cutting window 29. In addition to the use of a single beam, cutting path 51 may be established by plural beams from one or multiple energy beam sources (lasers) and may be stationary or scanned.

The parallel-to-the window geometry of the cutting path 51 provides two important aspects of the invention. First, it is very important from a safety standpoint, as it prevents the laser beam 55 from passing through the cutting window 29 to the environment outside the cutting edge enclosure 20. This ensures that the closed laser cutting device of the invention is completely non-invasive. If the laser beam were permitted to exit the cutting window, the user or other individual might undesirably be subjected to the potential danger of having the laser beam incident upon a portion of the body other than the hair being cut, such as the eyes, which may occur in an open laser system, described above.

Secondly, directing the laser beam 55 adjacent to and parallel to the entire length of the cutting window 29 serves to ensure that, regardless of where it is inserted in the cutting window 29, the material to be cut will always be intercepted by the laser beam 55. How much inserted material is then vaporized/cut by the laser beam 55 will depend upon its insertion depth through cutting window 29, the dimensions of the components, including the wall thickness of the cutting edge enclosure 20, the cross-section of the laser beam 55, and the spacing of the laser beam 55 relative to the interior wall surface of the cutting edge enclosure 20.

Although the embodiment of the invention shown in FIGS. 1–3 employs a cutting laser beam generator mounted and powered externally of the housing cavity, the laser itself may be installed within the housing 12 proper, as diagrammatically illustrated at 150 in the interior plan view of FIG. 4, and may be powered by batteries 160 mounted within a housing battery compartment for the purpose. The remainder of the cutting device is the same as the previous embodiment of FIGS. 1–3.

As pointed out above, an advantage of the use of an externally mounted laser, as in the embodiment of FIGS. 1–3, is the fact that it reduces the size of the cutting device, and also allows the laser to be independently powered and cooled. Thus, the first embodiment may be preferred for substantially higher optical power density applications, such as light industrial uses and professional salons, for example, whereas the second embodiment readily lends itself to consumer uses, such as personal cosmetic products.

As will be appreciated from the foregoing description, the drawbacks of conventional laser hair removal schemes are effectively obviated by the non-invasive laser beam-based cutting device of the present invention, which is configured to readily cut relatively small cross-section material, such as human or animal hair, without subjecting the underlying skin or any other portion of the subject or the surrounding environment to impingement and potential damage by the cutting beam.

As pointed out above, because the cutting path of the laser beam is aligned with and parallel to the longitudinal direction of the cutting window, then regardless of where it is inserted in the cutting window, the material (e.g., hair) to be cut will always be intercepted and cut by the laser beam. Yet, the beam cannot exit the cutting window to the environment outside the cutting edge enclosure, making the invention non-invasive and safe for consumer use. Among the benefits of the laser hair removal system of the present invention are the fact that the laser has a typical useful life of twenty thousand hours, yielding over twenty years worth of shaving performance. Also, there is no blade to sharpen or replace and no need for the use of shaving cream.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein, but intend to cover all such changes and modifications as are obvious to one of ordinary skill in the art.

What is claimed:

1. A device for severing an element comprising:

an enclosure having an aperture sized to accommodate entry of said element into an interior region of said enclosure; and an energy director disposed within said interior region of said enclosure and configured to direct energy that is sufficient to sever said element along a path on an enclosure-interior side of said aperture, while preventing said energy from exiting said aperture, and wherein said energy director includes an energy terminator that is configured to sink energy that has been directed across said aperture.

2. A device according to claim 1, wherein said energy comprises electromagnetic energy.

3. A device according to claim 1, wherein said energy director is configured to direct a beam of energy across said aperture.

4. A device according to claim 1, wherein said energy director is configured to direct an optical energy beam across said aperture.

5. A device according to claim 1, wherein said energy director is configured to direct a laser beam across said aperture.

6. A device according to claim 1, wherein said enclosure is sized to be hand-held, and said aperture is configured to accommodate entry of hair projecting from a body into said interior region of said enclosure and into said path of said energy, and wherein said energy director is arranged to direct said energy along said path so as to sever said hair in said interior region of said enclosure, while preventing entry of skin of said body into said path of said energy in said interior region of said enclosure.

7. A cutting device for severing an element, such as hair and the like projecting from the surface of a medium, such as body skin comprising:

a housing having an exterior which is placeable against said surface of said medium and having an aperture therethrough that is sized to accommodate passage of said element into an interior region of said housing, while preventing entry of said surface of said medium into said interior region of said housing; and an optical energy beam director disposed within said housing and being configured to direct a beam of optical energy along a path in said interior region of said housing, and thereby onto said element passing through said aperture into said interior region of said housing, thereby severing said element, while preventing said beam of optical energy from exiting said aperture, and wherein said optical energy beam director includes an energy terminator that is operative to sink said beam of optical energy downstream of said path.

8. A cutting device according to claim 7, wherein said beam of optical energy is a laser beam.

9. A cutting device according to claim 7, wherein said aperture is of a size sufficient to accommodate the thickness of said element to be severed, but not so large as to allow entry of an underlying support surface from which said element to be severed projects.

10. A cutting device according to claim 7, wherein said aperture is configured to include an interrupted surface that is operative to inhibit entry of undesirable material or foreign matter into the housing cavity, and to confine and orient said element in a direction that is generally transverse to said beam of optical energy.

11. A cutting device according to claim 7, wherein said optical energy beam director is arranged such that a cutting path of said beam of optical energy through said interior region of said housing is aligned with and parallel to said aperture, so as to prevent said beam from exiting said cutting device, and ensure that regardless of where said element is inserted through said aperture, said element is intercepted by said beam.

12. A cutting device, for severing an element, such as hair and the like projecting from the surface of a medium, such as body skin comprising:

a housing having an exterior which is placeable against said surface of said medium and having an aperture therethrough that is sized to accommodate passage of said element into an interior region of said housing, while preventing entry of said surface of said medium into said interior region of said housing; and an optical energy beam director disposed within said housing and being configured to direct a beam of optical energy along a path in said interior region of said housing, and thereby onto said element passing through said aperture into said interior region of said housing, thereby severing said element, while preventing said beam of optical energy from exiting said aperture, and wherein said housing has a forward end to which a cutting edge enclosure is attached, and an interior cavity in which a laser beam-supplying optical fiber and a light trap are installed, said optical fiber being coupled to receive a laser beam and being coupled with said optical energy beam director, said light trap being operative to absorb said laser beam traveling along a return path of said optical energy beam director after it has passed through said interior region of said housing and has severed said element, so that no portion of said laser beam exits said cutting device.

13. A method for severing an element, such as hair, fibers, and the like projecting from the surface of a medium, such as body skin comprising the steps of:

(a) providing an enclosure having an aperture sized to accommodate entry of said element into an interior region of said enclosure;

(b) inserting said element through said aperture into said interior region of said enclosure; and (c) directing energy sufficient to sever said element along a path passing through said interior region of said enclosure so that said element inserted through said aperture in step (b) is severed, while preventing said energy from exiting said aperture, and sinking energy that has been directed along said path.

14. A method according to claim 13, wherein said energy comprises electromagnetic energy.

15. A method according to claim 13, wherein said energy is a laser beam.

16. A method according to claim 13, wherein, in step (a), said aperture is configured to accommodate entry of said hair, fibers or the like projecting from a body into said interior region of said enclosure, and to prevent entry of skin of said body into said path of said energy in said interior region of said housing.

* * * * *